United States Patent
Steimecke et al.

(10) Patent No.: US 8,951,549 B2
(45) Date of Patent: Feb. 10, 2015

(54) METHOD FOR THE REDUCTION OF THE CONCENTRATION OF AMINES AND SALTS THEREOF

(75) Inventors: Günter Steimecke, Wernigerode (DE); Steffen Hoffmann, Schlanstedt (DE); Thomas Görner, Schlanstedt (DE)

(73) Assignee: Froximun AG, Schlanstedt (DE)

( * ) Notice: Subject to any disclaimer, the term of this patent is extended or adjusted under 35 U.S.C. 154(b) by 104 days.

(21) Appl. No.: 13/130,735

(22) PCT Filed: Nov. 16, 2009

(86) PCT No.: PCT/EP2009/065221
§ 371 (c)(1),
(2), (4) Date: May 23, 2011

(87) PCT Pub. No.: WO2010/057849
PCT Pub. Date: May 27, 2010

(65) Prior Publication Data
US 2011/0229588 A1    Sep. 22, 2011

(30) Foreign Application Priority Data

Nov. 21, 2008  (DE) .......................... 10 2008 043 959
Nov. 21, 2008  (DE) .......................... 10 2008 043 967

(51) Int. Cl.
*A61K 33/00*    (2006.01)
*C02F 1/42*     (2006.01)
(Continued)

(52) U.S. Cl.
CPC ................. *A61K 33/00* (2013.01); *C02F 1/281* (2013.01); *C02F 1/42* (2013.01); *C02F 2101/16* (2013.01)
USPC ........... 424/439; 424/442; 424/443; 424/447; 426/106; 426/132; 426/271; 502/60; 502/73; 502/86; 502/102; 564/1; 564/123; 564/229; 564/280; 564/305; 564/463

(58) Field of Classification Search
USPC ........ 426/271, 106, 132; 502/60, 73, 86, 102, 502/232, 250, 251; 564/1, 123, 229, 280, 564/305, 463; 424/439, 442
See application file for complete search history.

(56) References Cited

U.S. PATENT DOCUMENTS 4,380,669 A *  4/1983  Chang et al. .................. 564/402
7,108,784 B1    9/2006  Litz et al.
(Continued)

FOREIGN PATENT DOCUMENTS

WO    WO 2008/064249    5/2008

OTHER PUBLICATIONS

Sudnikovich et al., "Wastewater treatment using natural zeolites," 1985, Tsvetney Netally (Moscow, Russian Federation), vol. 9, pp. 90-91; Abstract only.*
"Amine Reactivity", MSU [online] updated May 5, 2013; [retrieved Oct. 19, 2013]; Retrieved from the InternetL <URL: http://www2.chemistry.msu.edu/faculty/reusch/VirtTxtJml/amine1.htm.*
(Continued)

*Primary Examiner* — Jane C Oswecki
(74) *Attorney, Agent, or Firm* — Ursula B. Day, Esq.

(57) ABSTRACT

The invention relates to a method for reducing the concentration of amines and salts thereof, wherein the amines have the general chemical formula I R1R2R3N and the salts have the formula II R1R2R3N—H, wherein the amines and salts thereof exist in aqueous solution or aqueous suspension and are brought into contact with clinoptilolitic or clinoptilolite-containing mixtures. The method itself is suitable for use in food preparation and in the manufacture of foods. The inventive idea of reducing the concentration of amines and salts thereof is also useful in the manufacture of medical products for absorbing and for removing amines from the intestinal tract or the skin area of humans and animals.

5 Claims, 1 Drawing Sheet

(51) Int. Cl.
*C02F 1/28* (2006.01)
*C02F 101/16* (2006.01)

(56) References Cited

U.S. PATENT DOCUMENTS

| | | | |
|---|---|---|---|
| 2005/0031708 A1* | 2/2005 | Portney | 424/684 |
| 2005/0106267 A1 | 5/2005 | Frykman et al. | |
| 2006/0292242 A1* | 12/2006 | Hraschan et al. | 424/618 |
| 2008/0044548 A1 | 2/2008 | Hale et al. | |
| 2009/0226492 A1* | 9/2009 | Danz et al. | 424/401 |
| 2009/0274796 A1* | 11/2009 | Yamka et al. | 426/87 |

OTHER PUBLICATIONS

"Amine Reactivity", MSU [online] updated May 5, 2013; [retrieved Oct. 19, 2013]; Retrieved from the Internet: <URL: http://www2.chemistry.msu.edu/faculty/reusch/VirtTxtJml/amine1.htm.*

Sprynskyy M et al.: Ammoniumsorption from aqueous solutions by the natural zeolite Transcarpathian clinoptilolite studied under dynamic conditions Journal of Colloid and Interface Science, Academic Press, New York, NY, US vol. 284, No. 2 Apr. 15, 2005 pp. 408-415.

* cited by examiner

METHOD FOR THE REDUCTION OF THE CONCENTRATION OF AMINES AND SALTS THEREOF

CROSS-REFERENCES TO RELATED APPLICATIONS

This application is the U.S. National Stage of International Application No. PCT/EP20091065221, filed Nov. 16, 2009, which designated the United States and has been published as International Publication No. WO 2010/057849and which claims the priority of German Patent Application, Serial No. 10 2008 043 967.3, filed Nov. 21, 2008 and German Patent Application, Serial No. 10 2008 043 959.2, filed Nov. 21, 2008, pursuant to 35 U.S.C. 119(a)-(d).

BACKGROUND OF THE INVENTION

The invention relates to a method for the reduction of the concentration of amines and salts thereof, wherein the amines have the general formula I $R^1R^2R^3N$, and the salts have the formula II $R^1R^2R^3N\text{—H}$. The method is suitable for use in food preparation and in the manufacture of foods. The inventive idea is also useful in the manufacture of medical products for absorbing and for removing amines from the digestive tract or skin area of humans or animals.

Structurally, amines are derived from ammonia wherein one, two or three hydrogen atoms of the ammonia can be substituted for same or different organic radicals. Amines and their salts have been known for a long time to chemists and are being used in various applications in the laboratory as well as for technical synthesis processes. Amines are also present in humans and animals. They serve as regulatory and control substances in such a vast number of biological processes that to date, their classification into substances that are either harmful, tending to be stressful, or even harmless is impossible and neither useful nor sensible. Rather, in order to judge whether a substance of a given concentration has a harmful or a rather harmless effect has to be determined for each substance individually in light of its biological effect and concentrations that are relevant for the organism. Further, a growing number of amines enters the human body either as pharmaceutically active substances in pharmaceutical products (for instance as blood pressure lowering substances), in trace amounts as herbicides or their remnants, or as contaminants in food products. An industrial, chemical processing of amines results among others in the synthesis of azo dyes: this class of dyes can be found almost everywhere in the human living space, including labels on technical installations, product packaging, or dying of foods, sometimes in trace amounts and sometimes in larger amounts. Other sources of amines are cooking, baking, grilling and frying processes, which are commonly used for the preparation of meals and represent mainly thermal processes. The amines are formed through reaction of amino acids with carbohydrates, fats and other reactants at high temperature. In addition, plants and their extracts contain significant amounts of amines. Examples are the large group of alkaloids, narcotic drugs, and toxins of mushrooms.

A further significant source of amines in humans or animals is digestion: under anaerobic conditions in the intestine proteins are broken down through the activity of bacterial acylases into shorter peptide sequences and eventually into amino acids which are normally resorbed through the intestine and used by the organism. However, some of these amino acids are either broken down into carbon dioxide and amine by bacterial amino acid decarboxylase or are further degraded through other steps. In the literature these amines are referred to as "biogenic amines".

A further significant source of amines is microbial activity. All foods produced by or through the use of microorganisms contain amines. Examples are cheese, wine, sauerkraut, beer, yogurt and kefir. In addition amines are also produced during the storage of meat, fish, sausages, poultry and game. Normally, the amount of amines increases strongly in cases where food is stored for too long or becomes spoiled. In these cases, beside the increasing microbial load, amine concentrations that were tolerable in the beginning become encumbering or toxic for the body. To avoid excessive amounts of encumbering bacterial amines, food should always be produced, prepared and consumed freshly. A critical situation arises, however, in cases where bacterial amines carry out the function of a tissue hormone which itself is involved in a specific regulatory function in human or animal organisms. In these cases the organism is forced to chemically alter the respective amine which is present in the chyme, completely in order to prevent its resorbtion through the intestinal mucosa into the body. Otherwise, uncontrollable reactions would occur which would override the organism's ability to initiate and control these reactions in the respective tissues. Such a chemical alteration is achieved by the ferment system monoamine oxidase or diamine oxidase respectively. The ferment system is able to break down a large number of mainly primary amines through hydrogen peroxide via oxidative deamination into the respective carbonyl compound and ammonia, and its activity in the intestinal mucosa is sufficiently high to allow higher organisms to protect themselves from biogenic amines. This reaction is an oxidative deamination with elimination of ammonia. It is the reverse reaction of the reductive amination, which is known in chemistry as Leukart-Wallach-reaction for about 100 years. Several factors can contribute to the reduction or, in rare cases almost complete loss of the diamino or aminooxidase activity in parts of the intestine of humans and animals, such as aging processes, enzyme defects, and pathological changes in the intestinal mucosa, numerous aminooxidase inhibiting drugs, as well as auxiliary materials and preservatives in food. For instance, in case of ingestion of uncontrolled amounts of 2-(4'-imidazolyl)-ethylamine, which functions as tissue hormone and neurotransmitter in the human body, the affected persons contract severe intestinal inflammation or multiple food intolerance. The course of the disease can span over years, sometimes decades and, because of the particular severity of the disease causes strong psychological stress. The number of affected persons has risen strongly in the last thirty years. In the case of the more common and less severe form of the disease, its cause is mostly not recognized and affected persons intermittently suffer from painful and quite unpleasant digestive complications. In the human and animal body 2-(4'-imidazolyl)-ethylamine plays a central role in allergic reactions and is involved in the defense against foreign substances and microorganisms through the immune system. 2-(4'-imidazolyl)-ethylamine is very important in the gastrointestinal tract for the regulation of gastric acid production as well as in the central nervous system for the regulation of the sleep-wake-rhythm. 2-(4'-imidazolyl)-ethylamine is stored in mast cells, basophile granulocytes and nerve cells. If needed 2-(4'-imidazolyl)-ethylamine can be released from mast cells and basophile granulocytes very rapidly as for instance in allergic reactions or after mechanical injuries. The physiological effect of 2-(4'-imidazolyl)-ethylamine is based on dilation of the small vessels which manifests itself in redness of the skin, increased permeability of vessels, and contraction of the smooth musculature in the bronchia, intestine, uterus and large vessels. The unwanted effects of allergic reactions include headache, runny nose, difficulty of breathing and asthma, and skin reactions such as itching and formation of wheals. Further, heart function is also influenced by 2-(4'-imidazolyl)-ethylamine which can manifest itself in tachycardia or arrhythmia. Blood pressure drops significantly. The effect on the gastro-intestinal tract consists of soft stool and diarrhea.

The most important function of the body's own 2-(4'-imidazolyl)-ethylamine is its participation in the defense against foreign substances and its pathological participation in the symptoms of allergies and asthma. Further, 2-(4'-imidazolyl)-ethylamine is a mediator substance in inflammations and burns. In these cases 2-(4'-imidazolyl)-ethylamine leads to itching and pain, contraction of the smooth musculature in the bronchia and the large blood vessels. An increased permeability of the vascular walls leads to urticaria. In addition, 2-(4'-imidazolyl)-ethylamine leads to the release of adrenaline. The body tries to guard against resorbtion of 2-(4'-imidazolyl)-ethylamine from the intestine by a high activity of the enzyme monoamine oxidase or diamine oxidase respectively, and by an as complete as possible degradation of 2-(4'-imidazolyl)-ethylamine.

Two further amines, which can be generated through microbial activity in the intestine during digestion are 2-phenyl-ethylamine and 2-(4'-hydroxyphenyl)-ethylamine. Resorbtion of 2-phenyl-ethylamine leads to a rise of blood sugar levels. At the same time 2-phenyl-ethylamine is an amphetamine derivative and thus an amine which causes addiction and increased appetite and, through sustained high blood sugar levels can lead to type II diabetes. It is commonly found in larger amounts in chocolate and the human body can produce it endogenously under certain circumstances. It is created in the intestine through bacterial degradation of the amino acid phenylalanine. 2-(4'-hydroxyphenyl)-ethylamine causes a strong rise of blood pressure through stimulation of the sympathetic nervous system. Systolic blood pressures of 250 to 300 mmHg caused by 2-(4'-hydroxyphenyl)-ethylamine are not uncommon. The health risks are easy to imagine and are commonly summarized with the term hypertonic crisis. 2-(4'-hydroxyphenyl)-ethylamine is generated from the amino acid tyrosine through bacterial degradation under the influence of decarboxylases.

A further, very important biologically active amine is dimethylamine, a secondary amine. It is generated in relatively large amounts in muscle tissue and reaches the intestine directly mainly through consumption of fish. It is also generated partly through bacterial degradation during digestion often with sarcosine as intermediate, but also as a result of trans-methylation reactions, involving for instance methionine. Increased concentrations of dimethylamine compromise neurophysiological functions. Especially in persons with limited kidney function and older age this circumstance is significant. Beside its property to lower blood pressure, diethylamine is able to react with nitrite, which is generated in the intestine through microbial reduction of nitrate which is present in drinking water or in consumed vegetables. The reaction of diethylamine with nitrite occurs spontaneously at pH 5.0 and is catalyzed in bacterial species at a pH of 7.2. The result of the reaction is dimethylnitrosamine, a highly carcinogenic substance which belongs to the group of nitrosamines. The majority of these nitrosamines have the ability to cause tumors in animal experiments. Thus, already 30 to 40 years ago dimethylamine was suspected to function as a potential pre carcinogen in humans and animals. The degradation of dimethylamine through aminooxidases in the intestinal mucosa is not possible, and therefore the entire amount of dimethylamine present or generated in the intestine is resorbed and distributed within the entire body through the bloodstream. Through the activity of the kidneys diethylamine becomes a component of the urine in healthy humans and can be excreted from the body. It can best be detected by gas chromatography, 1H-NMR-spectroscopy or photometrically in the urine. The predominant amount of dimethylamine is generated through degradation of methylated arginine. The healthy human being excretes about 17.5 milligrams of dimethylamine per day through urine. Males excrete 21.2 milligrams while females excrete 13.5 milligram on average.

A further important secondary amine is pyrrolidine. It can be generated through bacterial decarboxylation of the amino acid proline. As an amino acid proline is a component of proteins. In analogy to dimthylamine, pyrrolidine reacts with nitrite to form nitrosopyrrolidinee, a substance which is also highly carcinogenic. pyrrolidine was found in some organisms.

A number of other carcinogenic amines is generated in the intestine under strongly reducing conditions during digestion. Especially members of the group of azo dyes through splitting of the azo group form aromatic amines, such as benzidine, aniline and naphtylamine, or substituted derivatives thereof. The production and use of several of these aromatic amines has been banned. However, production and trade of azo dyes that are chemically accessible though these substances are still permitted internationally. The German industry has voluntarily abandoned production of these potentially dangerous azo dyes for several years. However, all azo dyes in question can still reach the internal market through imports of finished products, as long as no similar, as far as possible voluntary, production restrictions exist in countries of origin and production.

In analogy to the intestine, substances especially amines, can be taken up by the body through the skin: minor injuries, insect bites, abrasions, but also more severe injuries can become populated by infectious germs. The wounds become infected and some microorganisms are capable to release amines, especially 2-(4'-imidazolyl)-ethylamine, in this environment as well. The activity of the amine degrading oxidases is relatively lower compared to that in the intestinal mucosa. Partly, microorganisms are capable to produce additional toxic compounds which enter the surrounding tissue and in this way can destroy the tissue and lead to its lysis. The lyzed tissue in turn forms the basis for the microorganisms' further development and propagation. The wound becomes larger. The infection progresses. In many cases such infections are caused by the bacterium *Staphylococcus aureus*, which is commonly found on the skin or in the nose of humans. Many species of *Staphylococcus aureus* have become resistant to antibiotics. The result of the resistance against antibiotics is that treatment with one or with a combination of several antibiotics has little or no effect and the bacteria are still able to propagate in the wound. In this way the wounds continue to develop further and expand deeper into the tissue, until eventually a clinically effective antibiotic is found. If there is no effective antibiotic and none can be found in time, affected persons mostly die of ensuing sepsis.

The disulfidic cystamine, which is also a biogenic amine, has the characteristic to inhibit blood clotting and, in higher concentration, to prevent blood clotting altogether. In the 1960ies efforts were made to use this characteristic for the development of new inhibitors of thrombocyte aggregation. However, these efforts failed because of the formation of skin abscesses and lung complications. Moreover, cystamine leads to lack of appetite, drowsiness, increased salivation and lowers the blood glucose level. A number of diseases are connected to spontaneous bleeding, for instance in the intestine or other mucous membranes. Frequent spontaneous bleeding of mucous membranes for example in the intestine, nose or lung can have an infection as the underlying cause. If, after infection, cystamines are released in high concentrations and/or the human has pathological monoamine or diamine oxidase weaknesses with regard to cystamine in the affected tissues, spontaneous local bleeding or hemorrhaging into the tissue can occur due to local inhibition of blood clotting. Very strong bleedings of the mucous membranes occur in hemorrhagic fevers that flare up sporadically in the tropics. Lassa fever, Ebola fever and Dengue fever are mentioned here in particular. In addition, nosocomial infections play an increasing role and require the highest safety measures during treatment.

Tryptamine has the characteristic to cause nightmares in affected persons, when it reaches the blood stream through routes mentioned above. This is not surprising since tryptamine is structurally closely related to LSD=lysergic acid diethylamide. Tryptamine is often a natural component of heavy red wines and can sometimes also be found in good lager wines.

As can be seen from the above discussion, amines have the ability to influence the metabolism and with that the health of humans and animals. It is important in this context to realize that a reduction of enzymatic activity of the monoamine and diamine oxidases or generation of large amounts of amines in the intestine or through the skin, can lead to an uncontrolled assimilation of a large number of amines into the human or animal body. This can then lead to the health consequences mentioned above. A number of amines are not or only hardly degraded in the intestine, and others are even only produced in the intestine during digestion. This creates the task to develop a process to reduce the uptake of amines through the intestine or skin.

SUMMARY OF THE INVENTION

A part of this task consists in particular of providing a possibility for the production of a pharmaceutical agent for the effective reduction of the concentrations of amines in the intestine and on the skin.

The solution of the task that underlies the invention consists on the one hand in a process for the reduction of the concentration of amines and salts thereof, wherein the amines are described by the formula I $R^1R^2R^3N$ and their salts by the formula II $R^1R^2R^3N$—H, in which the amines and their salts are present in an aqueous solution or aqueous suspension and are brought into, contact with clinoptilolite or clinoptilolite containing mixtures.

According to the invention, the naturally occurring zeolite clinoptilolite is used. clinoptilolites are hydrated alumosilicates (zeolites) of the formula $(Ca, K_2, Na_2, Mg)_4Al_8Si_{40}O_{96} \cdot 24 H_2O$.

The natural occurrences consist to 84 percent of pure clinoptilolite. The further mineralogical composition is supplemented by:

Cristobalite: 8 percent;
Feldspar: 3 to 4 percent;
Illite: 4 percent;
Quarz: traces; and
Carbonate minerals

Chemically, the mineral is composed of the following oxides:

$SiO_2$ 65 to 71.3 percent;
$Al_2O_3$ 11.5 to 13.1 percent;
CaO 2.7 to 5.2 percent; . $K_2O$ 2.2 bis 3.4 percent;
$Fe_2O_3$ 0.7 to 1.9 percent;
MgO 0.6 to 1.2 percent;
$Na_2O$ 0.2 to 1.3 percent and
$TiO_2$ 0.1 to 0.3 percent.

The following physical data were determined:
Softening temperature: 1260° C.;
Melting temperature: 1340° C.;
Density: 2.2 to 2.5 g/cm$^3$;
Compressive strength: 33 Mpa; porosity: 32 to 40 percent;
Pore diameter: 0.4 nm and
Mohs hardness: 2.5 to 3.5.

The clinoptilolite has a gray-green color and is odorless. The basic skeleton of the clinoptilolite lattice consists of $SiO_2$-tetraeders and $Al_2O_3$. The ratio of silicon to aluminum in the case of clinoptilolite is 4:1. The crystal structures formed by oxygen bridges give rise to pores and canals. The surface area of the clinoptilolite is extraordinarily large, since in the interior of the lattice connected cavities exist in all three spacial dimensions. The exchange of tetravalant silicon atoms for trivalent aluminum atoms creates, a cation exchange capacity. This exchange causes a negative charge excess. The negative charges of the silicon/aluminum-tetraeders are compensated in the interior by mobile positive ions of the alkali and earth-alkanine elements (Ca, K, Na, Mg) that are stored in the cavities, as well as by larger amounts of stored water. A characteristic trait of zeolites is their exchange ability of bound ions for others (selectivity: $Cs^+>Pb^{2+}>NH_4^+>Cu^{2+}>Hg^{2+}>Cd^{2+}>Ni^{2+}>Co^{2+}$, $NH_4^+>K^+>Mg^{2+}>Ca^{2+}$). Its ion exchange capacity is 1.2 to 1.5 mole per kg. Among these $Ca^{2+}$ and $Mg^{2+}$ are the most dominant exchangeable cations of zeolite. They can be exchanged for other elements, for instance for deleterious elements such as lead, mercury and other heavy metals, as wells as for ammonium.

Smaller and middle sized molecules are also able to enter these cavities through the canals and to displace the mobile ions from their positions. Among these molecules are, surprisingly, the before mentioned amines of the formula I and salts of protonated amines of the formula II. The process according to the invention is particularly suited for the reduction of the concentration of amines and their corresponding salts, where the three radicals $R^1$, $R^2$ and $R^3$ of the formula I and II are maximally two hydrogen atoms and maximally three similar or different alkyl-, alkenyl-, aryl-, aralkyl-, polyaryl- or heterocylcic radicals which themselves can be substituted with similar or different radicals such as alkyl-, halogen-, $NH_2$—, acyl-NH—, aryl-NH—, heterocylyl-, OH, —SH and its oxidation products, —$SCH_3$, —CO—$NH_2$, —O—$CH_3$. Preferably, the process is applied to solutions or suspensions in which the compounds of the general formula I and formula II in the aqueous solution or suspension in water are in chemical equilibrium with each other by reaction with acid or by deprotonation in water:

$$R^1R^2R^3N \underset{-H^+}{\overset{+H^+}{\rightleftarrows}} R^1R^2R^3N\text{—}H.$$

Formula I         Formula II

For a better understanding of the process it should be added that all amines by reaction with water are converted to salts and, depending on the pH-value are present more in the amine form or the salt form respectively. It is an equilibrium reaction. At pH 6 to pH 7 most of the readily water soluble amines are predominantly present in the salt configuration. When mentioning amines in the present invention, this of course includes the corresponding salt of the amine, which can be incorporated into the lattice of the clinoptilolite.

In a particularly advantageous embodiment of the process according to the invention clinoptilolite or clinoptilolite containing mixtures are mechanically modified and activated by reduction in size of the particles before being brought into contact with the amines and/or their salts. In a preferred embodiment of the invention the particles of the clinoptilolite have a particle size between 2 and 16 µm, zeta potentials between 20 to 26 mV and a specific surface area between 30 and 60 m$^2$/g.

A preferred field of application of the process comprises the preparation of meals and the production of food to reduce the concentration of amines of the general formula I and/or their salts of the formula II in these meals or food. The reduction of the concentration of amines of the general formula I and/or salts of the formula II can be achieved by adding clinoptilolite or a clinoptilolite mixture before ingestion of the food, for instance during production or consumption of the food.

However, clinoptilolite can also be taken up separately in a defined amount at a particular point in time, optionally together with other substances. This allows for clinoptilolite or clinoptilolite containing mixtures to be used in the production of medical products for absorbing and removing amines of the general formula I $R^1R^2R^3N$ and/or their salts of the formula II $R^1R^2R^3N$—H, that are present in aqueous solution or aqueous suspension in the digestive tract or skin of humans and animals. According to the invention, the effect of such a medical product is based on the one hand on the fact that through its ingestion clinoptilolite is added or being brought into contact with chyme. Chyme means the mixture which results from the influence of digestive secretes, such as saliva and gastric juice, on the ingested food. Since chyme always contains water, amines bind to the clinoptilolite. Weakly bound ions such as calcium or manganese are given off into the chyme during digestion. clinoptilolite is a calcium aluminum silicate.

On the other hand clinoptilolite is not resorbed through the intestine or the skin after ingestion. Corresponding blood levels of clinoptilolite are not detectable. Overall, the effect of clinoptilolite is therefore based on the binding of amines or their salts, which are generated during digestion or were present in the chyme, to clinoptilolite followed by excretion through stool. Lack of resorbtion was shown through experiments using techetium-99. No radiation which would have been caused by resorbtion of clinoptilolite particles that had tightly bound technetium-99 was detected in the organs. Through the use of clinoptilolite according to the invention the organism is relieved of amines that mainly form during digestion or through the interaction of microorganisms with bodily tissue. A number of amines have a relatively high binding capacity for clinoptilolite. This binding capacity is in part significantly higher compared to ammonium or heavy metal ions. As mentioned before, clinoptilolite can be activated and modified by suitable mechanical processes, wherein the clinoptilolite particles are reduced in size in a way which results in a particle size between 2 and 16 µm, zeta potentials between 20 and 26 mV and a specific surface area between 30 and 60 m$^2$/g. For application on the skin, clinoptilolite dries out and eventually falls off together with chaff if present. In summary, in suitable applications clinoptilolite relieves the body of amines in the intestine or the skin.

In the case of dimethylamine, which is a component of urine in healthy humans and can be generated through bacterial degradation of creatine, application of clinoptilolite relieves the human and animal body of a substance which, under physiological conditions can react with nitrite to dimethylnitrosamine even without the influence of enzymes. This reaction also occurs spontaneously in vitro at pH-values around pH 5 and is catalyzed by many bacteria enzymatically at pH values around pH 7. For this reason, dimethylamine plays the role of a pre-carcinogen. Formation of nitrite also occurs through participation of bacteria. Bacteria in the intestine reduce nitrate to nitrite. However, nitrate is also generated through the metabolization of nitrogen monoxide, which the body produces endogenously to regulate blood pressure. Although uptake of nitrate can be reduced through drinking water which is free from or low in nitrate, nitrogen monoxide formation cannot be influenced to date, thus apparently limiting a possible influence on pre carcinogenesis to the nitrate/nitrite side.

The binding of dimethylammonium to clinoptilolite is exceptionally high, surprisingly significantly higher than the binding of ammonium to clinoptilolite. This new finding opens up the possibility to actively intervene in the process of pre-carcinogenesis and thus carcinogenesis itself through the use of clinoptilolite. At the same time, according to current knowledge, dimethylamine is quantity wise the main carcinogen in the human body. The present inventive concept can be used for the development of medical products, with the goal to relieve the body of dimethylamin/dimethylammonium and to prevent carcinogenesis by influencing pre-carcinogenesis. Surprisingly, other potential pre-carcinogens that also form nitrosamines with nitrite are bound by clinoptilolite as well. Among those are pyrrolidinee, β-hydroxypyrrolidinee and piperidine or their salts respectively. The first two mentioned amines can form through decarboxylation of the amino acids proline and hydroxyproline. So far it is not known how piperidine is formed. Even in the animal experiment, known cancer-causing substances such as aromatic amines are bound by clinoptilolite and thus removed from the chyme of the gut. These include the aromatic amines benzidine and aniline. But also 1,2-dimethylhydrazine, which can be used for induction of colon cancer in animal experiments, surprisingly, is reduced in its concentration by binding to the clinoptilolite. Thus, clinoptilolite removes carcinogenic as well as pre-carcinogenic substances from the chyme.

The reduction of the concentration of the primary amine 2-(4'-imidazolyl)-ethylamine by contact with clinoptilolite in the chyme of the intestine and on the skin and within wounds is of particular importance, since this compound is an important tissue hormone in the body. After bacterial infections, a number of germs use decarboxylation of the amino acid histidine, to produce large amounts of 2-(4'-imidazolyl)-ethylamine within the wound. These amounts far overwhelm the common oxidative degradation reactions of 2-(4'-imidazolyl)-ethylamine. This leads to intensive urticaria within the wound. The nettle secrete discharged by the body is an excellent source of nutrients for bacterial germs which causes the infection to increase significantly within the wound. Especially in the case of infections with methicillin resistant *Staphylococcus aureus* germs, (in the following abbreviated MRSA) this fact is important because in the case of MRSA infections resistances against common antibiotics arise which can complicate treatment significantly or make it impossible altogether. By applying clinoptilolite or a mixture of clinoptilolite and water several times to the cleaned wound and using sterile bandaging, the mechanism that includes the release of 2-(4'-imidazolyl)-ethylamine, the formation of nettle secrete and the increase of infection can surprisingly be interrupted. The MRSA germs and other 2-(4'-imidazolyl)-ethylamine releasing germs therefore lose their advantage over genetically "normal" *Staphylococcus aureus* and other germs that lack the ability to form 2-(4'-imidazolyl)-ethylamine. An organism without immune defects gains control over wound healing relatively quickly. A complete healing can begin. Initiated applications on animals were successful.

The reduction of the concentration of cystamine which can be present in the form of (2-aminoethyl)-disulfide-dihydrochloride, can also be achieved with clinoptilolite. Because of its ability to lower the concentration of cystamine which, as mentioned above inhibits blood clotting, clinoptilolite containing material that meets the appropriate hygienic standard can also stop minor bleedings and abrasions. The clinoptilolite coalesces with the forming chaff and, after healing, falls off together with the chaff. The visible speed of healing increases significantly.

DETAILED DESCRIPTION OF PREFERRED EMBODIMENTS

Further details, characteristics and advantages of the invention result from the drawings and the following description of examples of embodiments:
It shows.

Example 1

62.9 mg 2-(4'-hydroxyphenyl)-ethylamine-hydrochloride are dissolved to 50 ml in distilled water. 0.5 ml of this solution is diluted with water such that the concentration of 2-(4'-hydroxyphenyl)-ethylammonium is 40 mg/l. This solution is mixed with 500 mg clinoptilolite and stirred at 20° C. for 3.5 hours. After centrifugation of the reaction solution and clear filtration of the supernatant the concentration of the 2-(4'-hydroxyphenyl)-ethylammonium is determined. Result: The concentration of 2-(4'-hydroxyphenyl)-ethylammonium was lowered by 35.2 percent.

Example 2

62.9 mg 2-(4'-hydroxyphenyl)-ethylamine-hydrochloride are dissolved to 50 ml in distilled water. 0.5 ml of this solution is diluted with water such that the concentration of 2-(4'-hydroxyphenyl)-ethylammonium is 40 mg/l. This solution is mixed with 50 mg clinoptilolite and stirred at 20° C. for 7 hours. After centrifugation of the reaction solution and clear filtration of the supernatant the concentration of the 2-(4'-hydroxyphenyl)-ethylammonium is determined. From this the reduction of the 2-(4'-Hydroxyphenyl)-ethylammonium concentration is determined. Result: The concentration of 2-(4'-hydroxyphenyl)-ethylammonium was lowered by 13.2 percent.

Example 3

71.0 mg of 2-(4'-hydroxyphenyl)-ethylamine-hydrochloride are dissolved to 50 ml in distilled water. 0.5 ml of this solution is diluted with water such that the concentration of 2-(4'-hydroxyphenyl)-ethylammonium is 40 mg/l. This solution is mixed with 100 mg clinoptilolite material with a content of 44 percent and stirred at 37° C. for 3.5 hours. After centrifugation of the reaction solution and clear filtration of the supernatant the lowering of concentration of 2-(4'-hydroxyphenyl)-ethylammonium is determined. Result: the concentration of 2-(4'-hydroxyphenyl)-ethylammonium was lowered by 11.8 percent.

Example 4

45.3 mg of 2-(4'-hydroxyphenyl)-ethylamine-hydrochloride are dissolved to 50 ml in distilled water. 0.5 ml of this solution is diluted with water such that the concentration of 2-(4'-hydroxyphenyl)-ethylammonium is 40 mg/l. This solution is mixed with 500 mg clinoptilolite which was ground very finely in the laboratory mill beforehand, and stirred at 37° C. for 17 hours. After centrifugation of the reaction solution and clear filtration of the supernatant, the lowering of the concentration of 2-(4'-hydroxyphenyl)-ethylammonium is determined. Result: the concentration of 2-(4'-hydroxyphenyl)-ethylammonium was lowered by 38.0 percent.

Example 5

62.9 mg of 2-(4'-hydroxyphenyl)-ethylamine-hydrochloride are dissolved to 50 ml in distilled water. 0.5 ml of this solution is diluted with water such that the concentration of 2-(4'-hydroxyphenyl)-ethylammonium is 20.0 mg/l. This solution is mixed with 500 mg clinoptilolite material with a clinoptilolite content of 55 percent and stirred at 20° C. for 7 hours. After centrifugation of the reaction solution and clear filtration of the supernatant, the lowering of the concentration of 2-(4'-hydroxyphenyl)-ethylammonium is determined.

Example 6

55.7 mg of 2-(4'-hydroxyphenyl)-ethylamine-hydrochloride are dissolved to 50 ml in distilled water. 0.5 ml of this solution is diluted with water such that the concentration of 2-(4'-hydroxyphenyl)-ethylammonium is 20.0 mg/l. This solution is mixed with 500 mg clinoptilolite material with a clinoptilolite content of 55 percent. The solution is then shaken and let sit over night. After centrifugation of the reaction solution and clear filtration of the supernatant, the lowering of the concentration of 2-(4'-hydroxyphenyl)-ethylammonium is determined. Result: the concentration of 2-(4"-hydroxyphenyl)-ethylammonium was reduced by 29.1 percent

Example 7

18.2 mg of 1,2-dimethylhydrazine-dihydrochloride are dissolved to 50 ml in distilled water. 0.5 ml of this solution is diluted with water such that the concentration of 1,2-dimethylhydrazinium-dication is 40 mg/l. This solution is mixed with 500 mg clinoptilolite material with a clinoptilolite content of 80 percent and stirred at 20° C. for 3 hours. After centrifugation of the reaction solution and clear filtration of the supernatant the concentration of 1,2-dimethylhydrazinium-dication is determined. Result: The concentration of 1,2-dimethylhydrazinium-dication was reduced by 87.9 percent.

Example 8

18.2 mg of 1,2-dimethylhydrazine-dihydrochloride are dissolved to 50 ml in distilled water. 0.5 ml of this solution is diluted with distilled water such that the concentration of 1,2-dimethylhydrazinium-Dication is 40 mg/l. This solution is mixed with 50 mg clinoptilolite material with a clinoptilolite content of 89 percent and stirred at 20° C. for 7 hours. After centrifugation of the reaction solution and clear filtration of the supernatant, the concentration of 1,2-dimethylhydrazinium-dication is determined. Result: The concentration of 1,2-dimethylhydrazinium-dication was reduced by 28.5 percent.

Example 9

18.2 mg of 1,2-dimethylhydrazine-dihydrochloride are dissolved to 50 ml in distilled water. 0.5 ml of this solution is diluted with distilled water such that the concentration of 1,2-dimethylhydrazinium-dication is 10 mg/l. This solution is mixed with 50 mg technical clinoptilolite and stirred at 37° C. for 27 hours. After centrifugation of the reaction solution and clear filtration of the supernatant the concentration of the 1,2-dimethylhydrazinium-dication is determined. Result: the concentration of the 1,2-dimethylhydrazinium-dication was reduced by 48.5 percent.

Example 10

18.2 mg of 1,2-dimethylhydrazine-dihydrochloride are dissolved to 50 ml in distilled water. 0.5 ml of this solution is diluted with distilled water such that the concentration of the 1,2-dimethylhydrazinium-dication is 10 mg/l. This solution is mixed with 500 mg of clinoptilolite material and stirred at 20° C. for 6 hours. After centrifugation of the reaction solution and clear filtration of the supernatant the concentration of the 1,2-dimethylhydrazinium-dication is determined. Result: The concentration of the 1,2-dimethylhydrazinium-dication was reduced by >98 percent.

Example 11

19.0 mg bis-(2-aminoethyl)-disulfide-dihydrochloride are dissolved to 15 ml of distilled water. 0.5 ml of this solution is diluted with distilled water such that the concentration of bis-(2-aminoethyl)-disulfide-dication is 40 mg/l. This solution is mixed with 500 mg of clinoptilolite material and stirred at 20° C. for 90 minutes. After centrifugation of the reaction solution and clear filtration of the supernatant, the concentration of the bis-(2-aminoethyl)-disulfide-dication is determined. Result: The concentration of the bis-(2-aminoethyl)-disulfide-dication was reduced by >99 percent.

Example 12

19.0 mg of bis-(2-aminoethyl)-disulfide-dihydrochloride are dissolved to 15 ml in distilled water. 0.5 ml of this solution is diluted with distilled water such that the Concentration of the bis-(2-aminoethyl)-disulfide-dication is 40 mg/l. This solution is mixed with 50 mg of clinoptilolite material and stirred at 20° C. for 90 minutes. After centrifugation of the reaction solution and clear filtration of the supernatant, the concentration of the bis-(2-aminoethyl)-disulfide-dication is determined. Result: The concentration of the bis-(2-aminoethyl)-disulfide-dication was reduced by 80.6 percent.

Example 13

19 mg bis-(2-aminoethyl)-disulfide-dihydrochloride are dissolved to 15 ml in distilled water. 0.5 ml of this solution is diluted with distilled water such that the concentration of the bis-(2-aminoethyl)-disulfide-dication is 40 mg/l. This solution is mixed with 50 mg clinoptilolite material with a clinoptilolite content of 55 percent and stirred at 37° C. for 17 minutes. After centrifugation of the reaction solution and clear filtration of the supernatant the concentration of the bis-(2-aminoethyl)-disulfide-dication is determined. Result: the concentration of the bis-(2-aminoethyl)-disulfide-dication was reduced by 92.5 percent.

Example 14

19.0 mg of bis-(2-aminoethyl)-disulfide-dihydrochloride are dissolved to 15 ml in distilled water. 0.5 ml of this solution are diluted with distilled water such that the concentration of the bis-(2-ammonium-ethyl)-disulfide-dication is 10 mg/l. Into this solution, 50 mg of clinoptilolite are strewn through a powder funnel and the powder funnel is closed. The entire mixture is shaken well and let sit over night at 20° C. After centrifugation of the reaction solution and clear filtration of the supernatant the concentration of the cystamine-dication is determined. Result: The concentration of the cystamine-dication was reduced by 94 percent.

Example 15

19 mg bis-(2-amino-ethyl)-disulfide-dihydrochloride are dissolved in distilled water to 15 ml. 0.5 ml of this solution is diluted with distilled water such that the concentration of the bis-(2-ammonium-ethyl)-disulfide-dication is 20 mg/l. This solution is mixed with 500 mg clinoptilolite material and stirred at 20° C. for 30 minutes. After centrifugation of the reaction solution and clear filtration of the supernatant the concentration of the bis-(2-ammonium-ethyl)-disulfide-dication is determined. Result: the concentration of the bis-(2-ammonium-ethyl)-disulfide-dication was reduced by >99 percent.

Example 16

Figure 1:
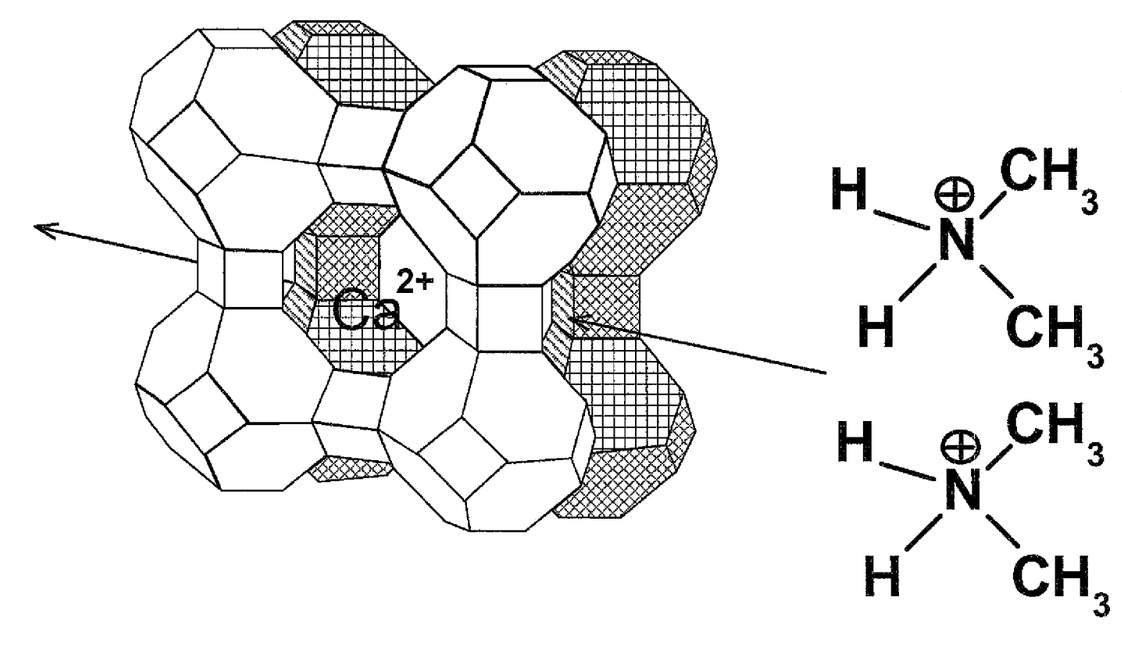
FIG. 1: A schematic representation of the ionic exchange on clinoptilolite.

15.6 mg dimethylamine-hydrochloride are dissolved in distilled water to 10 ml. As an example, FIG.1 schematically shows the exchange of $Ca^{2+}$ of a zeolite for a dimethylammonium ion. 0.5 ml of this solution is diluted with distilled water such that the concentration of the dimethylammonium cation is 40 mg/l. This solution is mixed with clinoptilolite material and stirred at 20° C. for 30 minutes. After centrifugation of the reaction solution and clear filtration of the supernatant the concentration of the dimethylammonium is determined. Result: The concentration of the dimethylammonium was reduced by 96.2 percent.

Example 17

15.6 mg dimethylamine-hydrochloride are dissolve in distilled water to 10 ml. 0.5 ml of this solution is diluted with distilled water such that the concentration of the dimethylammonium cation is 10 mg/l. This solution is mixed with clinoptilolite material and stirred at 20° C. for 90 minutes. After centrifugation of the reaction solution and clear filtration of the supernatant the concentration of the dimethylammonium was determined. Result: the concentration of the dimethylammonium was reduced by >99 percent.

Example 18

15.6 mg of dimethylamine-hydrochloride are dissolved in distilled water to 10 ml. 0.5 ml of this solution are diluted with distilled water such that the concentration of the dimethylammonium-cation is 20 mg/l. This solution is mixed with 500 mg clinoptilolite material and stirred at 37° C. for 19 hours. After centrifugation of the reaction solution and clear filtration of the supernatant the concentration of the dimethylammonium was determined. Result: the concentration of the dimethylammonium was reduced by >99 percent.

Example 19

13.5 mg of 2-(4'imidazolyl)-ethylamine-dihydrochloride are dissolved in distilled water to 10 ml. 0.5 ml of this solution is diluted with distilled water such that the concentration of 2-(4'imidazolyl)-ethylammonium-dication is 10 mg/l. This solution is mixed with 500 mg coarsely ground clinoptilolite material with a clinoptilolite content of 42 percent and stirred at 20° C. for 1 hour. After centrifugation of the reaction solution and clear filtration of the supernatant the concentration of the 2-(4' imidazolyl)-ethylammonium-dication is determined. Result: The reduction of the concentration of the 2-(4'imidazolyl)-ethylammonium-dication is 92 percent.

Example 20

13.3 mg tryptamine-hydrochloride are dissolved in distilled water to 25 ml. 0.5 ml of this solution is diluted with distilled water such that the concentration of the tryptamine-cation is 40 mg/l. This solution is mixed with 500 mg finely pulverized clinoptilolite and stirred at 19° C. for 1.5 hours. After centrifugation of the reaction solution and clear filtration of the supernatant, the concentration of the tryptamine cation is determined. Result: The concentration of the tryptamine cation was reduced by 79.5 percent.

Example 21

13.5 mg of 2-(4'imidazolyl)-ethylamine-dihydrochloride are dissolved in distilled water to 10 ml. 0.5 ml of this solution is are diluted with distilled water such that the concentration of the 2-(4'imidazolyl)-ethylammonium-dication is 40 mg/l. This solution is mixed with 500 mg clinoptilolite, with a content of 82 percent and stirred at 21° C. for 19 hours. After centrifugation of the reaction solution and clear filtration of the supernatant the concentration of the 2-(4'imidazolyl)-ethylammonium-dication is determined. Result: the concentration of the 2-(4'imidazolyl)-ethylammonium-dication was reduced by 84.6 percent.

Example 22

13.5 mg 2-(4'-imidazolyl)-ethylamine-dihydrochloride are dissolved in distilled water to 10 ml. 0.5 ml of this solution is diluted with distilled water such that the concentration of the 2-(4'imidazolyl)-ethylammonium-dication is 40 mg/l. This solution is mixed with 500 mg clinoptilolite and stirred at 20° C. for 1.5 hours. After centrifugation of the reaction solution and clear filtration of the supernatant the concentration of the 2-(4'imidazolyl)-ethylammonium-dication is determined. Result: The concentration of the 2-(4'imidazolyl)-ethylammonium-dication was reduced by 96.7 percent.

Example 23

13.3 mg of tryptamine-hydrochloride are dissolved in distilled water to 25 ml. 0.5 ml of this solution is diluted with distilled water such that the concentration of the tryptamine-cation is 40 mg/l. This solution is mixed with finely pulverized clinoptilolite and stirred at 19° C. for 1.5 hours. After centrifugation of the reaction solution and clear filtration of the supernatant the concentration of the tryptamine-cation is determined. Result: The concentration of the tryptamine-cation was reduced by 55.8 percent.

Example 24

13.5 mg of the 2-(4'imidazolyl)-ethylamine-dihydrochloride are dissolved in distilled water to 10 ml. 0.5 ml of this solution are diluted with distilled water such that the concentration of the 2-(4'imidazolyl)-ethylammonium-dication is 20 mg/l. This solution is mixed with 500 mg clinoptilolite and stirred at 20° C. for 3 hours. After centrifugation of the reaction solution and clear filtration of the supernatant the concentration of the 2-(4'imidazolyl)-ethylammonium-dication is determined. Result: The concentration of the 2-(4'imidazolyl)-ethylammonium-dication was reduced by 97.5 percent.

Example 25

18.5 mg tryptamine-hydrochloride are dissolved in distilled water to 25 ml. 0.5 ml of this solution is diluted with distilled water such that the concentration of the tryptamine-cation is 20 mg/l. This solution is mixed with 50 mg finely pulverized clinoptillolite and stirred at 19° C. for 1.5 hours. After centrifugation of the reaction solution and clear filtration of the supernatant the concentration of the tryptamine-cation is determined. Result: The concentration of the tryptamine-cation was reduced by 72.5 percent.

Example 26

20.5 mg tryptamine hydrochloride are dissolved in distilled water to 20 ml. 0.5 ml of this solution is diluted with distilled water such that the concentration of the tryptamine cation is 10 mg/l. This solution is mixed with 50 mg clinoptilolite and stirred at 37° C. for 6 hours. After centrifugation of the reaction solution and clear filtration of the supernatant, the concentration of the tryptamine cation is determined. Result: The concentration of the tryptamine cation was reduced by 89.9 percent.

Example 27

89.5 mg dimethylamine-hydrochloride are dissolved in distilled water to 50 ml. 0.5 ml of this solution is diluted with distilled water such that the concentration of the dimethylammonium cation is 40 mg/l. This solution is mixed with 50 mg clinoptilolite and stirred at 20° C. for 90 minutes. After centrifugation of the reaction solution and clear filtration of the supernatant the concentration of the dimethylammonium is determined. Result: the concentration of the dimethylammonium was reduced by 32.9 percent.

Example 28

54.4 mg 2-Phenylethylamine-hydrochloride are dissolved with distilled water to 50 ml. 0.5 ml of this solution is diluted with distilled water such that the concentration of the dimethylammonium-cation is 40 mg/l. This solution is mixed with 50 mg clinoptilolite and stirred at 20° C. for 90 minutes. After centrifugation of the reaction solution and clear filtration of the supernatant the concentration of the 2-phenylethyl-ammonium was determined. Result: The concentration of the 2-phenylehthyl-ammonium was reduced by 13.5 percent.

Example 29

54.4 mg of 2-phenylethylamine-hydrochloride are dissolved in distilled water to 50 ml. 0.5 ml of this solution is diluted with distilled water such that the concentration of the 2-phenylehthyl-ammonium cation is 40 mg/l. This solution is mixed with 500 mg of clinoptilolite and stirred at 20° C. for 90 minutes. After centrifugation of the reaction solution and clear filtration of the supernatant the concentration of the 2-phenylehthyl-ammonium is determined. Result: The concentration of the 2-phenylehthyl-ammonium was reduced by 75.2 percent.

Example 30

13.5 mg 2-(4'-imidazolyl)-ethylamine-dihydrochloride are dissolved in distilled water to 10 ml. 0.5 ml of this solution are diluted with distilled water such that the concentration of the 2-(4'-imidazolyl)-ethylammonium dication is 30 mg/l. This solution is mixed with 100 mg clinoptilolite and stirred at 20° C. for 30 minutes. After centrifugation of the reaction solution and clear filtration of the supernatant, the concentration of the 2-(4'-imidazolyl)-ethylammonium-dication was determined. Result: The concentration of the 2-(4'-imidazolyl)-ethylammonium-dication was reduced by >99 percent.

Example 31

52.8 mg 2-(4'-imidazolyl)-ethylamine-dihydrochloride are dissolved in distilled water to 50 ml. 0.5 ml of this solution is diluted with distilled water such that the concentration of the 2-(4'-imidazolyl)-ethylammonium-dichloride is 30 mg/l. This solution is mixed with 75 mg clinoptilolite and stirred at 20° C. for 40 minutes. After centrifugation of the reaction solution and clear filtration of the supernatant, the concentration of the 2-(4'-imidazolyl)-ethylammonium-dication was determined. Result: the concentration of the 2-(4'-imidazolyl)-ethylammonium-dication was reduced by 91.7 percent.

Example 32

13.5 mg 2-(4'-imidazolyl)-ethylamine-dihydrochloride are dissolved in distilled water to 10 ml. 0.5 ml of this solution is diluted with distilled water such that the concentration of the 2-(4'-imidazolyl)-ethylammonium-dichloride is 30 mg/l. Such a solution is mixed with 100 mg clinoptilolite and shaken at 20° C. for 30 minutes. After centrifugation of the reaction solution and clear filtration of the supernatant, the concentration of the 2-(4'-imidazolyl)-ethylammonium-dication was determined. Result: the concentration of the 2-(4'-imidazolyl)-ethylammonium-dication was reduced by >99 percent.

Example 33

114.5 mg pyrrolidine are weighed in a 50 ml volumetric flask. After dilution with distilled water 116 mg acetic acid are added and the flask filled up to the measure mark. 0.8 nil of the solution is diluted such that a concentration of pyrrolidine of 40 mg/l results. 12.5 ml of the solution are mixed with 0.5 g of clinoptilolite with the designation MANC and the mixture stirred at room temperature for 90 minutes. After centrifugation of the reaction solution and clear filtration of the supernatant the concentration of the pyrrolidine was determined. Result: The concentration of the pyrrolidine was reduced by 76.9 percent.

Example 34

9.5 mg Aniline are weighed in a 50 ml volumetric flask. After dilution with distilled water the necessary equivalent amount of pure hydrochloric acid is added and the flask filled up to the measure mark such that a concentration, of anilinium of 40 mg/l results. An aliquot of this solution is mixed with 0.5 g of clinoptilolite with the designation MANC and the mixture stirred at room temperature for 120 minutes. After careful separation of the reaction solution and clear filtration of the supernatant the concentration of aniline is determined. Result: The concentration of annilinium was reduced by 49 percent.

Example 35

17.65 mg benzidine-dihydrochloride are weighed in a 50 ml volumetric flask. After dilution distilled water is added and the flask filled to the measure mark. Afterwards, 0.5 ml of the solution are diluted such that a concentration of benzidinium-dication of 40 mg/l is generated. The solution is then mixed with 0.5 g of clinoptilolite and stirred at room temperature for 90 minutes. After immediate separation of the reaction solution and clear filtration of the supernatant, the concentration of benzidine is determined. Result: the concentration of benzidine was reduced by 98.4 percent.

What is claimed is:

1. A method for the reduction of a concentration of amines and their salts in a human comprising the steps of:
contacting the amines and/or their salts present in an aqueous solution in the digestive tract of the human with clinoptilolite or clinoptilolite containing mixtures to thereby reduce the concentration of the amines and/or their salts, wherein said amines are one or more of the group consisting of 2-(4'-imidazolyl)-ethylamine, 2-phenyl-ethylamine, 2-(4'-hydroxyphenyl) -ethylarmine, dimethylamine, (2-aminoethyl)-disulfide-dihydrochloride, 1,2-dimethylhydrazine, sarcosine pyrrolidine, benzidine, dimethylnitrosamine, aniline, naphtylamine, piperidine, disulfidic cystamine, tryptamine, dimethyl ammonium, and benzylidine, any of which can be substituted with the same or different radicals, that are selected from the group consisting of alkyl-, halogen-, $NH_2-$, acyl-NH—, aryl-NH—, heterocylyl-, OH, —SH and its oxidation products, $—SCH_3$, $—CO—NH_2$, and $—O—CH_3$.

2. The method of claim 1, wherein the amines and/or their salts in aqueous solution or aqueous suspension are in chemical equilibrium with each other through reaction with acid or through deprotonation in water.

3. The method as in claim 1, wherein the clinoptilolite comprises particles, in a particle size between 2 and 16 μm, has zeta potentials between 20 and 26 mV and a specific surface area between 30 and 60 m²/g.

4. A method for the reduction of a concentration of amines and their salts in a skin wound in a human comprising the steps of:
providing clinoptilolite or a mixture of clinoptilolite and water,
applying the clinoptilolite or a mixture of clinoptilolite and water several times to a cleaned wound using sterile bandaging to interrupt the formation of nettle secretion and release therefrom of 2-(4'-imidazolyl)-ethylamine by infection-causing bacteria.

5. A method of using clinoptilolite or clinoptilolite containing mixtures in preparation of meals or production of food stuff for humans comprising,
mixing, food stuff with clinoptilolite or the clinoptilolite containing mixtures, which after ingestion of food by a human, lowers a concentration of amines with a general formula I $R^1R^2R^3N$ and/or their salts of a formula II $R^1R^2R^3N$—H, present in aqueous solution or aqueous suspension in the chyme of a digestive tract wherein said amines are one or more of the group consisting of 2-(4'-imidazolyl)-ethylarnine, 2-phenyl-ethylamine, 2-(4'-hydroxyphenyl)-ethylamine dimethylamine, (2-amino-ethyl)-disulfide-dihydrochloride, 1,2-dimethylhydrazine, sarcosine pyrrolidine, benzidine, dimethylnitrosamine, aniline, naphtylamine, piperidine, disulfidic cystamine, tryptamine, dimethyl ammonium, and benzylidine, any of which can be substituted with the same or different radicals, that are selected from the group consisting of alkyl-, halogen-, $NH_2$—, acyl-NH—, aryl-NH—, heterocylyl-, OH, —SH and its oxidation products, —$SCH_3$, —CO—$NH_2$, and —O—$CH_3$.

* * * * *